United States Patent [19]

Robinson et al.

[11] Patent Number: 5,766,957

[45] Date of Patent: Jun. 16, 1998

[54] SPECTROPHOTOMETRIC TECHNIQUES

[75] Inventors: Grenville Arthur Robinson, Ealing, United Kingdom; Alan Derek Cookson, Boston, Mass.

[73] Assignee: Applied Research Systems Ars Holding, N.V., Curacao, Netherlands

[21] Appl. No.: 716,213

[22] PCT Filed: Mar. 9, 1995

[86] PCT No.: PCT/GB95/00507

§ 371 Date: Nov. 22, 1996

§ 102(e) Date: Nov. 22, 1996

[87] PCT Pub. No.: WO95/24632

PCT Pub. Date: Sep. 14, 1995

[30] Foreign Application Priority Data

Mar. 10, 1994 [GB] United Kingdom ............... 9404749

[51] Int. Cl.⁶ .................................................. G01N 27/26
[52] U.S. Cl. ................. 436/165; 422/82.09; 422/82.11; 356/246; 356/440
[58] Field of Search .......................... 422/82.09, 82.11; 436/164, 165, 180, 171; 356/246, 440

[56] References Cited

U.S. PATENT DOCUMENTS

| | | |
|---|---|---|
| 3,431,424 | 3/1969 | Allen . |
| 4,810,658 | 3/1989 | Shanks et al. ............... 436/172 |
| 4,978,503 | 12/1990 | Shanks et al. ............... 422/58 |
| 5,141,868 | 8/1992 | Shanks et al. ............... 435/288 |
| 5,273,633 | 12/1993 | Wang . |

FOREIGN PATENT DOCUMENTS

| | | |
|---|---|---|
| 0171148 | 2/1986 | European Pat. Off. . |
| 9014590 | 11/1990 | WIPO . |

OTHER PUBLICATIONS

Analytical Chemistry, vol. 55, No. 6, 1983 Easton Pennsylvania, USA, pp. 951–955, Wei Lai et al. "Determination of phosphorus in natural waters by long capillaryC cell absorption spectrometry".

*Primary Examiner*—Jeffrey Snay
*Attorney, Agent, or Firm*—Ostrolenk, Faber, Gerb & Soffen, LLP

[57] ABSTRACT

The use as a cuvette in spectrophotometric assays of a sample-collecting device is disclosed, the said device possessing a cavity or cavities each having a dimension small enough to enable sample liquid to be drawn into the cavity by capillary action, wherein a surface of the cavity is a surface of a transparent solid plate having a substantially rectangular cross section and forming a wall of the cavity, the opposite surface of the cavity being an additional structure having a substantially rectangular cross section and forming a wall of the cavity, and wherein a portion of said plate carries a reflective coating and a portion of said additional structure is reflective.

8 Claims, 2 Drawing Sheets

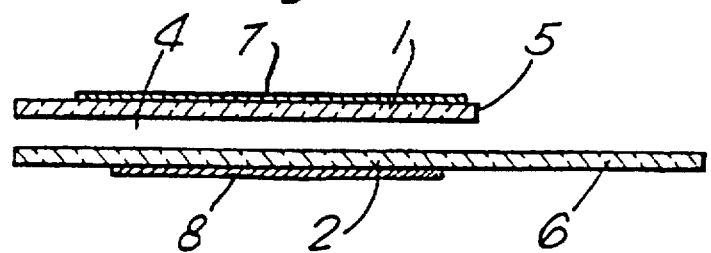
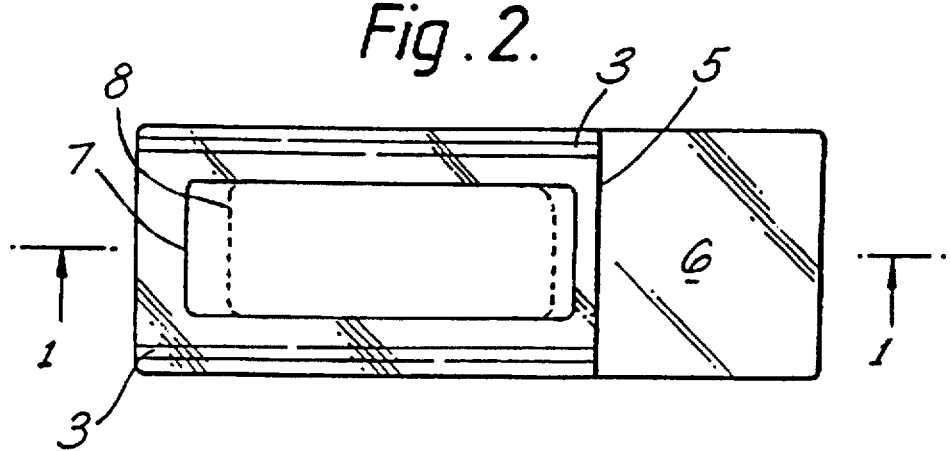

SPECTROPHOTOMETRIC TECHNIQUES

BACKGROUND OF THE INVENTION

The present invention relates to spectrophotometric techniques using particular devices.

In EP-A-0171148, devices are disclosed for use in chemical (especially biochemical or clinical) test procedures, particularly for use in specific binding assay procedures. The devices typically possess a cavity into which sample liquid is drawn. One surface of the cavity is a surface of a transparent solid plate which acts as a light transmissive waveguide; for use in specific binding assays, this surface carries an immobilised reagent appropriate to the assay to be carried out in the device. The plate has an edge which is substantially optically smooth and transverse to the plane of the plate and in use in an assay procedure the device can transmit, for example, fluorescence from an adsorbed fluorescent material along the plate acting as a waveguide, transfer of useful light across the boundary of the plate occurring by the evanescent wave located very close to the interface.

We have now found that devices similar to those in EP-A-0171148 may be used as a cuvette in spectrophotometric assays. In the normal mode of use of the devices as described in EP-A-0171148, there is only a thin film of sample (typically of the order of 0.1 mm) present in the device; passing radiation through a path length of this dimension is not suitable for reliable spectrophotometric measurement. We have now found, however, that totally internally reflecting radiation within a modified form of the device allows the radiation to pass through the sample many times and therefore enables a suitable path length (for example, of up to 1 cm) to be built up. Such a path length is then suitable for reliable spectrophotometric measurement.

Devices for analysing substances and which employ multiple internal reflection are already known. In U.S. Pat. No. 5,273,633 (Tiansong Wang), a device for capillary zone electrophoresis is disclosed which comprises a long transparent capillary tube with a reflecting surface surrounding the outer surface of the capillary, the reflecting surface having an incident and exit window for the electromagnetic radiation. Similarly, in Analytical Chem., vol 55, no. 6, 1983, pp 951–955 (Wei Lei et al), a long capillary cell, in which in use multiple internal reflection of electromagnetic radiation occurs, is employed for the colorimetric determination of phosphorus. U.S. Pat. No. 3,431,424 (Henry W. Allen) discloses a complex optical fluid sampling device which in use also empoys multiply reflected radiation.

These prior art devices are all based on a circular geometry and this presents certain disadvantages. As specifically acknowledged in U.S. Pat. No. 5,273,633, the fact that radial reflection occurs places constraints on the size and orientation of the incident window and also, since the exiting radiation will be distributed around the entire circumference of the capillary, on the preferred shape of the exit window and the detection apparatus. Furthermore, these prior art devices are relatively large (of the order of 50–100 cm) and this makes them impractical for use in routine analytical work. The use according to the present invention of a device as described above (the modified form of the device disclosed in EP-A-0171148) overcomes these disadvantages.

DESCRIPTION OF THE INVENTION

Thus, according to one aspect of the present invention, we provide the use of a sample-collecting device as a cuvette in spectrophotometric assays, the device possessing a cavity or cavities each having a dimension small enough to enable sample liquid to be drawn into the cavity by capillary action, wherein a surface of the cavity is a surface of a transparent solid plate having a substantially rectangular cross-section and forming a wall of the cavity, the opposite surface of the cavity being an additional structure having a substantially rectangular cross-section and forming a wall of the cavity, and wherein a portion of said plate carries a reflective coating and a portion of said additional structure is reflective.

According to a further aspect of the present invention there is provided a method of spectrophotometric assay of a species in a liquid sample using a device as defined above which comprises (a) filling said device with the sample liquid;

(b) irradiating said device with light from a suitable light source such that the radiation is totally internally reflected within said device; and (c) monitoring the radiation emerging from said device by conventional methods in order to determine whether and/or the extent to which the species is present in the sample.

Preferably the additional structure of the device is also a transparent plate a portion of which carries a reflective coating. However, this is not a necessary requirement and it is suitable merely to use a structure part of which is fabricated of an appropriate reflective material; in such an embodiment the material concerned is preferably inert with regard to the sample liquid to be contained within the cavity.

The reflective coating carried on the or each transparent plate is preferably carried on the external surface i.e. the surface remote from the cavity. However, the coating on the or each transparent plate may instead be carried on the internal surface i.e. the surface opposite the external surface (being that which forms part of the capillary cavity wall). Alternatively, where two transparent plates are present, one may carry the coating on the external surface whereas the other may carry the coating on the internal surface.

The reflective portions of the transparent plate and of the additional structure facilitate total internal reflection of radiation within the device in use in order to build up a suitable path length of the radiation through the sample.

The choice of where the reflective coating is carried on the or each transparent plate is made in the light of this result to be achieved.

A suitable coating for the transparent plate(s) is a metal coating as conventionally used in the preparation of coated glass, e.g. an aluminium coating.

The devices for use according to the present invention are conveniently manufactured, enable convenient sample collection by virtue of their capillarity and are especially suitable for handling and accurately metering small liquid samples, the volume of the cavity containing the sample being of the order of 0.1 ml in typical embodiments.

The devices for use according to the present invention may be constructed by similar methods to those described in detail for the devices of EP-A-0171148, but with the additional step of applying a reflective coating to the appropriate surface of the transparent plate(s).

Thus, typically a process for manufacturing sample-collecting devices as described hereinbefore would comprise the steps of (a) applying a coating of reflective material to a portion of a surface of a transparent sheet material which is to provide part of a multiplicity of the devices;

(b) either prior to or subsequent to step (a), attaching to said sheet material in parallel, spaced relation thereto an additional structure which together with said sheet material provides for each device of the multiplicity of devices a cavity of capillary dimension for collecting and retaining by capillarity a volume of sample liquid, a portion of the additional structure being reflective; and (c) separating the assembled laminate into portions each providing one or a plurality of the sample-collecting devices.

Where the additional structure is a transparent sheet material, a portion of which carries a coating of reflective material, an additional step would comprise the application of this coating.

The orientation of the attachment in (b) will determine on which surfaces (external or internal) of the cavity the coating (s) of reflective material is(are) carried.

The transparent plate(s) of the device for use according to the present invention may be fabricated from a variety of materials which can be transparent to infrared, visible and/or ultraviolet light depending on the spectrophotometric method to be carried out using the device. Suitable materials are, for example, glass e.g. sheet soda glass about 1 mm thick, silicas and plastics sheet material e.g. acrylic plastics material as well as materials conventionally used in the fabrication of spectroscopic cells such as quartz, NaCl and $CaF_2$. Where part of the additional structure is simply fabricated from a reflective material, this may, for example, be a chemically inert reflective metal such as gold or platinum.

A number of modifications of the devices as disclosed in detail in EP-A-0171148 are applicable to the device for use according to the present invention including for example the use of a barrier for selective takeup of sample liquid into the cavity, the use of a collection surface of the device onto which a drop of sample liquid can be placed and the provision of a fixed or releasable holder for the device. The present invention extends to the use of devices as described above incorporating such features.

The sample-collecting device as defined above would be used in conventional spectrophotometric detection methods and would find particular utility in the detection and determination of chemical moieties in biological samples. For example the devices are able to draw up a very small sample of blood e.g. from a finger spot and thus analysis of such a sample for routine moieties including haemoglobin, glucose and urea is envisaged.

In certain test methods, ancillary reagents may be needed and these can be dosed separately, or they can be carried in dry releasable form on a part of the device to be contacted in use by sample liquid e.g. a surface of the capillary cavity or a surface of a filter, if present. Such techniques are illustrated in EP-A-0171148.

BRIEF DESCRIPTION OF THE DRAWINGS

FIG. 1 shows a diagrammatic section through a device according to one embodiment of the invention.

FIG. 2 shows a diagrammatic plan of the device of FIG. 1, and includes a line I—I to show the line of section of FIG. 1.

Figure 3:
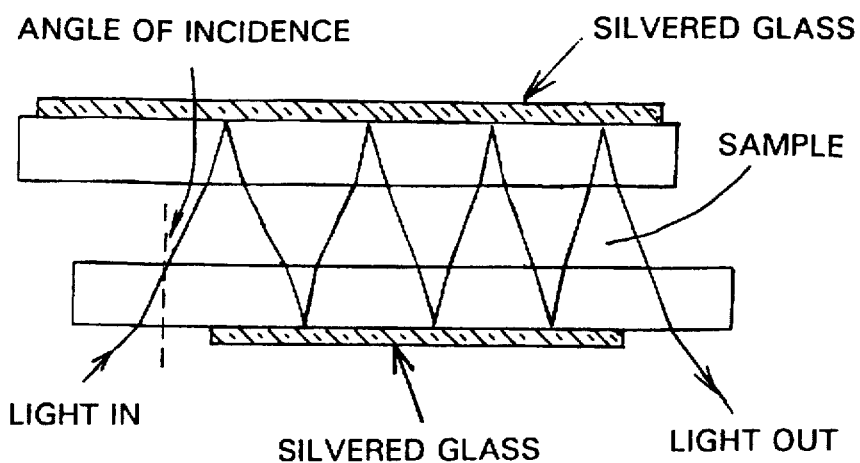
FIGS. 3 and 4 show schematically the use of the device according to the invention.

The device illustrated in FIGS. 1 and 2 comprises a transparent plate 1 and a transparent plate 2 fixed together in parallel opposed and spaced relation, preferably less than 1 mm apart, by bonding tracks 3 of suitable (e.g. epoxy) adhesive to form a capillary cell cavity 4, open at both ends, which communicates with the outside though a first discontinuity in the bonding 3 arranged to form a cell aperture at side 5 of plate 1. Another discontinuity is present at the other end of bonding 3, to leave another aperture, to allow exit of air when a sample liquid is loaded into the cell. Plate 2 has a portion 6 extending away from the aperture which acts as a platform or threshold or lip onto which a drop of sample liquid can be applied, so that this liquid can be made to fill the capillary cell cavity 4 by capillary flow. Cavity 4 attracts and contains a definite and adequately reproducible volume of liquid when loaded in this way. On a portion of each external surface of both plate 1 and plate 2 are respectively carried reflective coatings 7 and 8.

In the manufacture of such a device, the coating of the outside surfaces of the plates is carried out by conventional methods e.g. by the use of a vacuum and evaporation of a suitable metal such as silver or aluminium. The sealing is preferably achieved by screen printing onto one plate lines of epoxy resin which suitably comprise solid particles to ensure the desired spacing (e.g. substantially monodisperse ballotini). The two sheets are then brought together, subjected to vacuum and the adhesive cured by ultraviolet illumination. The plates are then scribed and broken into individual cell units.

Devices for use according to the present invention are preferably fabricated with a gap of between 0.1 mm and 1 mm, preferably to 0.5 mm, more preferably about 0.2 mm. The transparent plate(s) preferably have a thickness of between 0.5 and 1.5 mm, more preferably about 1.0 mm. The devices are also preferably fabricated so that in use in spectrophotometric assays the path length of the radiation through the sample is between 0.1 and 2.0 cm, more preferably about 1.0 cm. The devices are preferably of a length between 20 mm and 60 mm, more preferably about 40 mm, and have a width of between 5 mm and 20 mm, more preferably about 10 mm.

Thus, according to a further aspect of the present invention we provide a sample-collecting device as defined above in which the device has a length of between about 20 mm and 60 mm, a width of between about 5 mm and 20 mm and a gap between the transparent plate and the additional structure of about 0.1 mm to 1 mm.

FIG. 3 schematically illustrates the use of a device according to the present invention in spectrophotometric measurement, the incoming radiation being internally reflected in the device and exiting after a suitable path length has been built up.

The path length through the sample would be controlled by the length of the device, the thickness of the plates, the positioning of the reflective metal layers on the surfaces of the device and the angle of incidence of the radiation. Placing one or both of the coatings on the internal surface of the plate(s) as opposed to the external surface would also affect the overall path length, since it would alter the skip distance for each bounce of radiation within the device.

For example, for a device as illustrated in FIG. 3 where the width of each transparent plate is 1.1 mm and the angle of incidence of the radiation is 20°, each bounce of the light would result in a skip distance of approximately 1.75 mm (4.8×tan 20°) down the device with the light path through the sample being approximately 0.42 mm. Thus a device of this type which is at least 35 mm long would have a path length through the sample of at least 0.8 cm. In practice the device would be slightly longer, for example in the region of 40 mm, to allow for ease of handling. Assuming that the internal width of the device is 10 mm (between the bonding tracks) then the sample volume would be approximately 80 µl.

Figure 4:
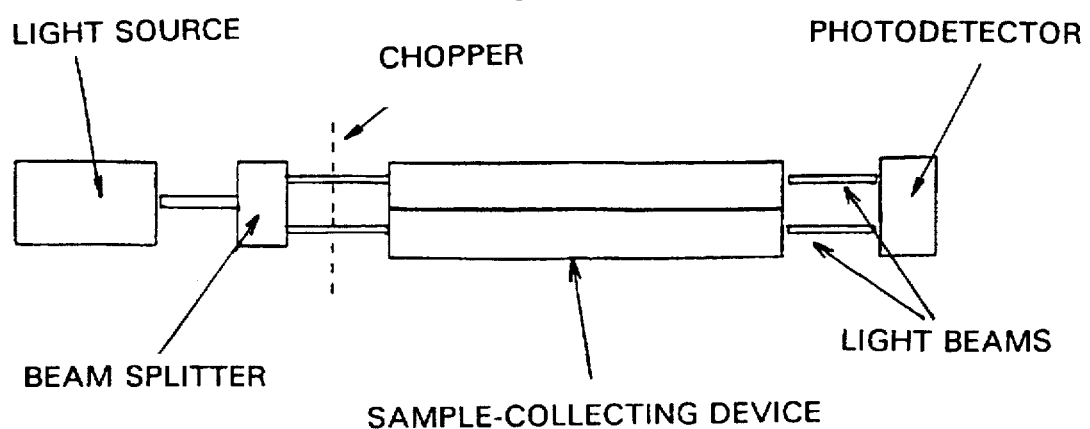

As an alternative configuration it is possible to allow for a sample and reference beam within the device, as illustrated schematically in FIG. 4. Ideally one light source which is split into two and chopped would be used to illuminate both sides of the device. The device would be formed with two separate cavities, one cavity containing the sample of interest and through which the sample beam travels, the other cavity containing the reference solution (essentially the 'solvent' of the sample solution) through which the reference beam passes. As an alternative, two distinct and separate devices could be used akin to a conventional double beam spectrophotometric technique. In either case, the use of a single detector is beneficial to avoid the problems of matching more than one detector.

We claim:

1. A method of spectrophotometric assay of a species in a liquid sample using a sample-collecting device comprising a cavity or cavities each having a dimension small enough to have a sample liquid drawn into the cavity by capillary action, wherein a surface of the cavity is a surface of a transparent solid plate having a substantially rectangular cross-section and forming a wall of the cavity, the opposite surface of the cavity is an additional structure having a substantially rectangular cross-section and forming a wall of the cavity, and wherein a portion of said plate carries a reflective coating and a portion of said additional structure is reflective, said method comprising (a) filling said device with the sample liquid;

(b) irradiating said device with light from a suitable light source such that the radiation is totally internally reflected within said device; and (c) monitoring the radiation emerging from said device in order to determine whether and optionally the extent to which the species is present in the sample.

2. A method as claimed in claim 1 wherein the additional structure of the device is also a transparent plate having a portion of which carries a reflective coating.

3. A method as claimed in claim 1 wherein a reflective coating is on an external surface of said plate.

4. A cuvette as claimed in claim 1, wherein a reflective coating is on each external surface of said plate.

5. A method as claimed in claim 1 wherein the device has a length of between about 20 mm and 60 mm, a width of between about 5 mm and 20 mm and a gap between the transparent plate and the additional structure of about 0.1 and 1 mm.

6. A method as claimed in claim 5, wherein the length is about 40 mm, the width is about 10 mm and the gap is about 0.1 to 0.5 mm.

7. A method as claimed in claim 6, wherein the additional structure of the device is a second transparent plate having a portion of which which carries a reflecting coating.

8. A method as claimed in claim 7, wherein a reflecting coating is on each external surface of said second plate.

* * * * *